United States Patent
He et al.

(10) Patent No.: US 11,484,478 B2
(45) Date of Patent: Nov. 1, 2022

(54) METHOD FOR MAKING COMPOSITION FOR ENAMEL REGENERATION

(71) Applicants: Xi'an University of Science and Technology, Shaanxi (CN); Yunnan Baiyao Group Health Product Co., Ltd., Yunnan (CN)

(72) Inventors: Yongjun He, Shaanxi (CN); Kegong Ning, Yunnan (CN)

(73) Assignees: XI'AN UNIVERSITY OF SCIENCE AND TECHNOLOGY, Shaanxi (CN); YUNNAN BAIYAO GROUP HEALTH PRODUCT CO., LTD., Yunnan (CN)

( * ) Notice: Subject to any disclaimer, the term of this patent is extended or adjusted under 35 U.S.C. 154(b) by 25 days.

(21) Appl. No.: 17/126,898

(22) Filed: Dec. 18, 2020

(65) Prior Publication Data
US 2021/0251859 A1    Aug. 19, 2021

(30) Foreign Application Priority Data
Feb. 13, 2020   (CN) .......................... 202010089792.X

(51) Int. Cl.
| | | |
|---|---|---|
| *A61Q 11/00* | (2006.01) | |
| *A61K 8/06* | (2006.01) | |
| *A61K 8/92* | (2006.01) | |
| *A61K 8/9706* | (2017.01) | |
| *A61K 8/9783* | (2017.01) | |
| *A61K 8/04* | (2006.01) | |
| *A61K 8/19* | (2006.01) | |
| *A61K 8/24* | (2006.01) | |
| *A61K 8/25* | (2006.01) | |
| *A61K 8/26* | (2006.01) | |
| *A61K 8/27* | (2006.01) | |
| *A61K 8/28* | (2006.01) | |
| *A61K 8/44* | (2006.01) | |
| *A61K 8/46* | (2006.01) | |
| *A61K 8/60* | (2006.01) | |
| *A61K 8/73* | (2006.01) | |
| *A61K 8/81* | (2006.01) | |
| *A61K 8/86* | (2006.01) | |
| *A61K 8/96* | (2006.01) | |

(52) U.S. Cl.
CPC .............. *A61K 8/066* (2013.01); *A61K 8/042* (2013.01); *A61K 8/19* (2013.01); *A61K 8/24* (2013.01); *A61K 8/25* (2013.01); *A61K 8/26* (2013.01); *A61K 8/27* (2013.01); *A61K 8/28* (2013.01); *A61K 8/44* (2013.01); *A61K 8/463* (2013.01); *A61K 8/602* (2013.01); *A61K 8/731* (2013.01); *A61K 8/8117* (2013.01); *A61K 8/8147* (2013.01); *A61K 8/86* (2013.01); *A61K 8/92* (2013.01); *A61K 8/922* (2013.01); *A61K 8/925* (2013.01); *A61K 8/965* (2013.01); *A61K 8/9706* (2017.08); *A61K 8/9783* (2017.08); *A61Q 11/00* (2013.01); *A61K 2800/412* (2013.01); *A61K 2800/413* (2013.01); *A61K 2800/52* (2013.01)

(58) Field of Classification Search
CPC ............ A61K 2300/00; A61K 2800/92; A61K 8/062; A61K 8/064; A61K 8/24; A61K 2800/412; A61K 8/066; A61K 8/06; A61Q 11/00
See application file for complete search history.

(56) References Cited

U.S. PATENT DOCUMENTS

| | | | | |
|---|---|---|---|---|
| 2013/0090392 A1* | 4/2013 | Pradhan | ................... | A23D 7/02 426/602 |
| 2018/0133119 A1* | 5/2018 | Rajaiah | ................... | A61K 8/31 |

* cited by examiner

*Primary Examiner* — Tracy Liu
(74) *Attorney, Agent, or Firm* — Dickinson Wright PLLC

(57) ABSTRACT

A method for making a composition for enamel regeneration proposes to encapsulate soluble calcium and phosphate salts within corresponding internal water phases in respective water-in-oil-in-water emulsions stabilized by solid particles, and add them to a toothpaste, enamel restoring gel or mouth wash base. In this way, the soluble calcium and phosphate salts can be present stably in the toothpaste, enamel restoring gel or mouth wash over a long period of time. When the toothpaste, enamel restoring gel or mouth wash of the present disclosure is used in oral cavity, the water-in-oil-in-water emulsions rapture under the effect of friction and pressing, releasing the soluble calcium and phosphate salts encapsulated within the corresponding internal water phases. As a result, the liquid in the user's oral cavity will contain high concentrations of calcium and phosphate ions, which can enhance the rate of enamel remineralization.

6 Claims, No Drawings

METHOD FOR MAKING COMPOSITION FOR ENAMEL REGENERATION

TECHNICAL FIELD

The present disclosure is generally related to the field of household chemicals, or the medical, care or cleaning field associated with oral hard tissues, and in particular to a composition for enamel regeneration, that is a medical composition, in particular an oral care composition capable of cleaning the teeth and/or oral cavity. The present disclosure further relates to a method for making the composition.

BACKGROUND

Enamel is the hardest tissue in the human body. Fully formed enamel consists of approximately 96% by weight of hydroxyapatite, 3% by weight of water, and 1% by weight of proteins and lipids. As the outer covering of the tooth, the enamel is always subject to physical attacks including occlusion, friction and wear, and to chemical attacks such as corrosion caused by acids that are produced by food or bacteria. Generally, in the case that the pH of the mouth is less than 5.5, hydroxyapatite, the major mineral component of the enamel, may dissolve, causing demineralization of the enamel.

Calcium and phosphate ions present in the saliva can buffer the variation of the pH value of the saliva to some extent, inhibiting the dissolution of hydroxyapatite. In the case that the saliva has a pH value greater than 5.5 and contains high concentrations of calcium and phosphate ions, calcium phosphate would be produced for tooth remineralization. However, typically, the concentrations of the calcium and phosphate ions are too low in the saliva to produce sufficient amount of hydroxyapatite to restore demineralized enamel.

Calcium and phosphate salts contained in the toothpaste, in the enamel restoring gel or in the mouth wash can lead to increased concentrations of calcium and phosphate ions in the oral environment during brushing of teeth, which can promote the remineralization of the teeth. However, if the calcium and phosphate salts contained in a toothpaste, enamel restoring gel or mouth wash have a low solubility, they may provide the oral environment with low concentrations of calcium and phosphate ions in use. If the calcium and phosphate salts contained in a toothpaste, enamel restoring gel or mouth wash have a high solubility, the calcium ions and the phosphate ions contained therein may react rapidly with each other to form a precipitate due to the fact that calcium phosphate, dicalcium phosphate, hydroxyapatite and the like have a low solubility product. Thus, in this case, the toothpaste, enamel restoring gel or mouth wash will still have low concentrations of free calcium and phosphate ions. Accordingly, adding calcium and phosphate salts to a toothpaste, enamel restoring gel or mouth wash base directly can only provide low concentrations of free calcium and phosphate ions, which may lead to a low rate of enamel remineralization during limited tooth brushing time and at limited tooth brushing frequency.

SUMMARY

An objective of the present disclosure is to provide a method for making a composition for enamel regeneration which can enable the liquid in a user's oral cavity to have high concentrations of calcium and phosphate ions when being used and thus enable an increased rate of enamel remineralization.

The objective of the disclosure is realized by a method for making a composition for enamel regeneration, comprising:

(1) Preparation of a Water-In-Oil-In-Water Emulsion Containing a Soluble Calcium Salt and Stabilized by Solid Particles, the Preparation of the Emulsion Comprising:

adding organic and/or inorganic micro-nano particles suitable for stabilizing emulsions to a natural oil of plant, animal or mineral origin, or to a synthetic oil produced from petrochemical products or products extracted from natural sources and mixing with stirring at 30 to 80° C. until homogeneous to form an oil phase, wherein, a mass ratio of the micro-nano particles (solid particles) to the natural or synthetic oil is from 0.1:100 to 25:100, and either the natural oil or the synthetic oil is suitable for oral care or for use in the preparation of a toothpaste, mouth wash or enamel restoring gel;

adding to water a substance capable of dissolving in water or alcohol and of supplying free calcium ions so as to form an aqueous solution with a calcium ion concentration of 0.1 to 60%;

mixing the aqueous solution with the oil phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil emulsion;

adding to water organic and/or inorganic micro-nano particles suitable for stabilizing emulsions to form a water phase, wherein, a mass ratio of the micro-nano particles to the water is from 0.1:100 to 25:100; and mixing the water-in-oil emulsion with the water phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil-in-water emulsion containing a soluble calcium salt;

(2) Preparation of a Water-In-Oil-In-Water Emulsion Containing a Soluble Phosphate Salt and Stabilized by Solid Particles, the Preparation of the Emulsion Comprising:

adding organic and/or inorganic micro-nano particles suitable for stabilizing emulsions to a natural oil of plant, animal or mineral origin, or to a synthetic oil produced from petrochemical products or products extracted from natural sources and mixing with stirring at 30 to 80° C. until homogeneous to form an oil phase, wherein, a mass ratio of the micro-nano particles (solid particles) to the natural or synthetic oil is from 0.1:100 to 25:100, and either the natural oil or the synthetic oil is suitable for oral care or for use in the preparation of a toothpaste, mouth wash or enamel resorting gel:

adding to water a substance capable of dissolving in water or alcohol and of supplying free phosphate, hydrogen phosphate, and/or dihydrogen phosphate ions so as to form an aqueous solution, with a concentration of the phosphate, hydrogen phosphate, and/or dihydrogen phosphate ions being 0.1 to 60%;

mixing the aqueous solution with the oil phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil emulsion;

adding to water organic and/or inorganic micro-nano particles suitable for stabilizing emulsions to form a water phase, wherein, a mass ratio of the micro-nano particles (solid particles) to the water is from 0.1:100 to 25:100; and mixing the water-in-oil emulsion with the water phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil-in-water emulsion containing a soluble phosphate salt;

(3) Preparation of a Mouth Wash, Toothpaste or Enamel Restoring Gel Containing Both a Soluble Calcium Salt and a Soluble Phosphate Salt, the Preparation Thereof Comprising:

mixing the water-in-oil-in-water emulsion containing a soluble calcium salt and the water-in-oil-in-water emulsion containing a soluble phosphate salt with a mouth wash, toothpaste, or enamel restoring gel base, with a stirring speed of 10 to 24,000 rpm at 30 to 80° C. for 0.5 to 120 minutes to obtain a mouth wash, toothpaste or enamel restoring gel containing both a soluble calcium salt and a soluble phosphate salt, wherein, a molar ratio of the calcium ions in the water-in-oil-in-water emulsion containing a soluble calcium salt to the phosphate ions in the water-in-oil-in-water emulsion containing a soluble phosphate salt is 5:3, and the ratio of the mass of the water-in-oil-in-water emulsion containing a soluble calcium salt and the water-in-oil-in-water emulsion containing a soluble phosphate salt to mass of the mouth wash, toothpaste or enamel restoring gel base is from 1:19 to 19:1.

The solid particles (micro-nano particles) used in the steps (1) and (2) may be one or more of silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, zeolite, polyethylene, polystyrene, a polyacrylic resin, a natural vegetable powder, a surface modified natural vegetable powder, and cellulose and a functionalized amphiphilic derivative thereof.

Alternatively, the solid particles may be one or more of silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, and zeolite modified with a silane coupling agent, a titanate coupling agent or a surfactant.

The surfactant for modifying the solid particles may be any amphiphilic surfactant suitable for use in the preparation of oral cleaning or care products, or combinations of such amphiphilic surfactants, including, but not limited to, sodium lauryl sulfate, sodium dodecyl benzene sulfate, sodium lauryl sulfate, a glucoside nonionic surfactant, betaine, and combinations thereof.

The oil used in the steps (1) and (2) may be one or more of rapeseed oil, peanut oil, cannabis oil, corn oil, olive oil, camellia oil, palm oil, sunflower oil, soybean oil, sesame oil, linseed oil, grape seed oil, walnut oil, peony seed oil, coconut oil, edible paraffin, turpentine, lard oil, beef fat, mutton fat, fish oil, oviductus ranae, snake oil, silicone oil, linear alkane, lipid, and alcohol non-miscible in water.

The substance capable of supplying free calcium ions may be one or more of calcium chloride, calcium carbonate, calcium hydroxide, calcium oxide, calcium phosphate, calcium nitrate, calcium gluconate, calcium bicarbonate, calcium bisulfate, and calcium lactate.

The substance capable of supplying free phosphate, hydrogen phosphate, and/or dihydrogen phosphate ions may be one or more of potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate.

In contrast to prior art, the present disclosure proposes to encapsulate the soluble calcium and phosphate salts within corresponding internal water phases in respective water-in-oil-in-water emulsions stabilized by solid particles, and add them to a toothpaste, enamel restoring gel or mouth wash base. In this way, the calcium and phosphate salts can be present stably in the toothpaste, enamel restoring gel or mouth wash over a long period of time. When the toothpaste, enamel restoring gel or mouth wash of the present disclosure is used in oral cavity, the water-in-oil-in-water emulsions rupture under the effect of friction and pressing, releasing the soluble calcium and phosphate salts encapsulated within the corresponding internal water phases. As a result, the liquid in the user's oral cavity will contain high concentrations of calcium and phosphate ions, which can enhance the rate of enamel remineralization.

DETAILED DESCRIPTION

Embodiments of the present disclosure will now be further described by way of examples.

Example 1

(1) Preparation of a Water-In-Oil-In-Water Emulsion Containing a Soluble Calcium Salt and Stabilized by Solid Particles 0.1 g of silicon dioxide was added to 100 g of rapeseed oil and mixed with stirring while heating until homogeneous to form an oil phase. During this, the mixture was heated to 30° C. Thereafter, 0.5 ml of a 0.1 wt. % calcium chloride solution and 9.5 ml of the rapeseed oil containing the silicon dioxide were mixed with a high-speed disperser at a stirring speed of 10 rpm and at 80° C. for 120 minutes to obtain a water-in-oil emulsion.

1 g of silicon dioxide was added to 100 g of water to form a water phase. 0.5 ml of the water-in-oil emulsion obtained above and 9.5 ml of the water phase were mixed with a high-speed disperser at a stirring speed of 24,000 rpm and at 30° C. for 0.5 minutes to obtain a water-in-oil-in-water emulsion containing a soluble calcium salt.

(2) Preparation of a Water-in-Oil-in-Water Emulsion Containing a Soluble Phosphate Salt and Stabilized by Solid Particles 0.1 g of silicon dioxide was added to 100 g of rapeseed oil and mixed with stirring while heating until homogeneous to form an oil phase. During this, the mixture was heated to 80° C. Thereafter, 0.5 ml of a 0.1 wt. % potassium phosphate solution and 9.5 ml of the rapeseed oil containing, the silicon dioxide were mixed with a high-speed disperser at a stirring speed of 10 rpm and at 30° C. for 120 minutes to obtain a water-in-oil emulsion.

0.1 g of silicon dioxide was added to 100 g of water to form a water phase. 0.5 ml of the water-in-oil emulsion obtained above and 9.5 ml of the water phase were mixed with a high-speed disperser at a stirring speed of 24,000 rpm and at 80° C. for 0.5 minutes to obtain a water-in-oil-in-water emulsion containing a soluble phosphate salt.

(3) Preparation of a Toothpaste Base

A toothpaste base was prepared by the known procedure using the following ingredients: a friction agent, a humectant, a surfactant, a thickening agent, a sweetener, a preservative, an active additive and a pigment.

(4) Preparation of a Toothpaste Containing Both a Soluble Calcium Slat and a Soluble Phosphate Salt 0.5 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being 5:3) and 9.5 g of the toothpaste base were mixed with a high-speed disperser at a stirring speed of 24,000 rpm and at 30° C. for 0.5 minutes to produce a toothpaste product.

Tests showed that a rate of enamel remineralization provided by the toothpaste in this Example was 52 times that provided by the conventional toothpaste containing hydroxyapatite.

Example 2

Toothpastes were prepared in the same manner as in Example 1 except that:—the solid particles was any organic, inorganic, or natural polymer material suitable for use in the preparation of oral cleaning or care products other than silicon dioxide, including, but not limited to, one of: aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, zeolite, polyethylene, polystyrene, a polyacrylic resin, a natural vegetable powder, a surface modified natural vegetable powder, and cellulose and a functionalized amphiphilic derivative thereof, or at least two of: silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, zeolite, polyethylene, polystyrene, a polyacrylic resin, a natural vegetable powder, a surface modified natural vegetable powder, and cellulose and a functionalized amphiphilic derivative thereof, or one or more of silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, and zeolite modified with a silane coupling agent, a titanate coupling agent or a surfactant; wherein, the surfactant used herein for modifying the solid particles was one or more of sodium lauryl sulfate, sodium dodecyl benzene sulfate, sodium lauryl sulfate, a glucoside nonionic surfactant, betaine, and the like;—the soluble calcium salt used was any substance capable of directly or indirectly supplying free calcium ions, including, but not limited to, one of calcium carbonate, calcium hydroxide, calcium oxide, calcium phosphate, calcium nitrate, calcium gluconate, calcium bicarbonate, calcium bisulfate, and calcium lactate, or at least two of: calcium chloride, calcium carbonate, calcium hydroxide, calcium oxide, calcium phosphate, calcium nitrate, calcium gluconate, calcium bicarbonate, calcium bisulfate, and calcium lactate;—the soluble phosphate salt used was one of: sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate, or at least two of: potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate;—and the oil used was any nonpolar substance suitable for oral care, including, but not limited to, one of peanut oil, cannabis oil, corn oil, olive oil, camellia oil, palm oil, sunflower oil, soybean oil, sesame oil, linseed oil, grape seed oil, walnut oil, peony seed oil, coconut oil, edible paraffin, turpentine, lard oil, beef fat mutton fat, fish oil, oviductus ranae, snake oil, silicone oil, linear alkane, lipid, and alcohol non-miscible in water, or at least two of: rapeseed oil, peanut oil, cannabis oil, corn oil, olive oil, camellia oil, palm oil, sunflower oil, soybean oil, sesame oil, linseed oil, grape seed oil, walnut oil, peony seed oil, coconut oil, edible paraffin, turpentine, lard oil, beef fat, mutton fat, fish oil, oviductus ranae, snake oil, silicone oil, linear alkane, lipid, and alcohol non-miscible in water.

Tests showed that a rate of enamel remineralization provided by the toothpastes in this Example was 32 to 60 times that provided by the conventional toothpaste containing hydroxyapatite.

Example 3

(1) Preparation of a Water-in-Oil-in-Water Emulsion Containing a Soluble Calcium Salt and Stabilized by Solid Particles 0.5 g of calcium carbonate was added to 2 g of sunflower oil and mixed with stirring while heating until homogeneous to form an oil phase. During this, the mixture was heated to 80° C. Thereafter, 1.5 ml of a 60 wt. % calcium nitrate solution and 1 ml of the sunflower oil containing the calcium carbonate were mixed with a high-speed disperser at a stirring speed of 24,000 rpm and at 30° C. for 0.5 minutes to obtain a water-in-oil emulsion.

1 g of calcium carbonate was added to 4 g of water and stirred until homogeneous to form a water phase. 1.5 ml of the water-in-oil emulsion obtained above and 1 ml of the water phase were mixed with a high-speed disperser at a stirring speed of 300 rpm and at 80° C. for 120 minutes to Obtain a water-in-oil-in-water emulsion containing calcium ions.

(2) Preparation of a Water-in-Oil-in-Water Emulsion Containing a Soluble Phosphate Salt and Stabilized by Solid Particles 0.5 g of calcium carbonate was added to 2 g of sunflower oil and mixed with stirring while heating until homogeneous to form an oil phase. During this, the mixture was heated to 30° C. Thereafter, 1.5 ml of a 60 wt % potassium dihydrogen phosphate solution and 1 ml of the sunflower oil containing the calcium carbonate were mixed with a high-speed disperser at a stirring speed of 24,000 rpm and at 80° C. for 0.5 minutes to obtain a water-in-oil emulsion.

1 g of calcium carbonate was added to 4 g of water and stirred until homogeneous to form a water phase. 1.5 ml of the water-in-oil emulsion obtained above and 1 ml of the water phase were mixed with a high-speed disperser at a stirring speed of 300 rpm and at 30° C. for 120 minutes to obtain a water-in-oil-in-water emulsion containing phosphate ions.

(3) Preparation of an Enamel Restoring Gel Base

Art enamel restoring gel base was prepared by the known procedure using the following ingredients: a friction agent, a humectant, a surfactant, a thickening agent, a sweetener, a preservative, an active additive and a pigment.

(4) Preparation of an Enamel Restoring Gel Containing Both a Soluble Calcium Slat and a Soluble Phosphate Salt 4 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being 5:3) and 0.2 g of the enamel restoring gel base were mixed with a high-speed disperser at a stirring speed of 300 rpm and at 80° C. for 120 minutes to produce an enamel restoring gel product containing both a soluble calcium slat and a soluble phosphate salt.

Tests showed that a rate of enamel remineralization provided by the enamel restoring gel in this Example was 45 times that provided by the conventional toothpaste containing hydroxyapatite.

Example 4

Enamel restoring gels were prepared in the same manner as in Example 3 except that:—the solid particles was any solid particles suitable for oral care other than those used in Example 3, including, but not limited to, one or more of: silicon dioxide, aluminium oxide, bioactive glass, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, zeolite, polyethylene, polystyrene, a polyacrylic resin, a natural vegetable powder, a surface modified natural vegetable powder, and cellulose and a functionalized amphiphilic derivative thereof, or at least two of: silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, zeolite, polyethylene, polystyrene, a polyacrylic resin, a natural vegetable powder, a surface modified natural vegetable powder, and cellulose and a functionalized amphiphilic derivative thereof, or one or more of: silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, and zeolite modified with a silane coupling agent, a titanate coupling agent or a surfactant; wherein, the surfactant used herein for modifying the solid particles was one or more of sodium lauryl sulfate, sodium dodecyl benzene sulfate, sodium lauryl sulfate, a glucoside nonionic surfactant, and betaine;—the soluble calcium salt used was any substance capable of directly or indirectly supplying free calcium ions, including, but not limited to, one of calcium carbonate, calcium hydroxide, calcium oxide, calcium phosphate, calcium gluconate, calcium bicarbonate, calcium bisulfate, and calcium lactate, or at least two of calcium chloride, calcium carbonate, calcium hydroxide, calcium oxide, calcium phosphate, calcium nitrate, calcium gluconate, calcium bicarbonate, calcium bisulfate, and calcium lactate;—the soluble phosphate salt used was one of: sodium phosphate, ammonium phosphate, potassium hydrogen phosphate, sodium hydrogen phosphate, ammonium hydrogen phosphate, sodium dihydrogen phosphate, and ammonium dihydrogen phosphate, or at least two of: potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate;—and the oil used was any nonpolar substance suitable for oral care, including, but not limited to, one of: rapeseed oil, peanut oil, cannabis oil, corn oil, olive oil, camellia oil, palm oil, soybean oil, sesame oil, linseed oil, grape seed oil, walnut oil, peony seed oil, coconut oil, edible paraffin, turpentine, lard oil, beef fat, mutton fat, fish oil, oviductus ranae, snake oil, silicone oil, linear alkane, lipid, and alcohol non-miscible in water, or at least two of rapeseed oil, peanut oil, cannabis oil, corn oil, olive oil, camellia oil, palm oil, sunflower oil, soybean oil, sesame oil, linseed oil, grape seed oil, walnut oil, peony seed oil, coconut oil, edible paraffin, turpentine, lard oil, beef fat, mutton fat, fish oil, oviductus ranae, snake oil, silicone oil, linear alkane, lipid, and alcohol non-miscible in water.

Tests showed that a rate of enamel remineralization provided by the enamel restoring gels in this Example was 23 to 83 times that provided by the conventional toothpaste containing hydroxyapatite.

Example 5

(1) Preparation of a Water-In-Oil-In-Water Emulsion Containing a Soluble Calcium Salt and Stabilized by Solid Particles 0.2 g of zinc oxide was added to 50 g of olive oil and mixed with stirring while heating until homogeneous to form an oil phase. During this, the mixture was heated to 30° C. Thereafter, 2.5 ml of a 2 wt. % calcium gluconate solution and 7.5 ml of the olive oil containing the zinc oxide were mixed with a high-speed disperser at a stirring speed of 6,000 rpm and at 30° C. for 40 minutes to obtain a water-in-oil emulsion.

2 g of calcium phosphate was added to 25 g of water and stirred while heating until homogeneous to form a water phase. During this, the mixture was heated to 30° C. 3 ml of the water-in-oil emulsion obtained above and 2 ml of the water phase were mixed with a high-speed disperser at a stirring speed of 4,000 rpm and at 30° C. for 20 minutes to obtain a water-in-oil-in-water emulsion containing calcium ions.

(2) Preparation of a Water-in-Oil-in-Water Emulsion Containing a Soluble Phosphate Salt and Stabilized by Solid Particles 0.6 g of calcium carbonate modified with a silane coupling agent was added to 10 g of peanut oil and mixed with stirring while heating until homogeneous to form an oil phase. During this, the mixture was heated to 30° C. Thereafter, 2 ml of a 5.5 wt. % sodium hydrogen phosphate solution and 5 ml of the peanut oil containing the modified hydroxyapatite were mixed with a high-speed disperser at a stirring speed of 18,000 rpm and at 30° C. for 10 minutes to obtain a water-in-oil emulsion.

1.2 g of magnesium hydroxide was added to 10 g of water to form a water phase. 3 ml of the water-in-oil emulsion obtained above and 5 ml of the water phase were mixed with a high-speed disperser at a stirring speed of 5,000 rpm and at 30° C. for 40 minutes to obtain a water-in-oil-in-water emulsion containing phosphate ions.

(3) Preparation of a Mouth Wash Base

A mouth wash base was prepared by the known procedure using the following ingredients: a humectant, a surfactant, a thickening agent, a sweetener, a preservative, an active additive, a flavor and the like.

(4) Preparation of a Mouth Wash Containing Both a Soluble Calcium Slat and a Soluble Phosphate Salt 3 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being 5:3) and 3 g of the mouth wash base were mixed with a high-speed disperser at a stirring speed of 9,000 rpm and at 30° C. for 15 minutes to produce a mouth wash product.

Tests showed that a rate of enamel remineralization provided by the mouth wash in this Example was 24 times that provided by the conventional mouth wash.

Example 6

(1) Preparation of a Water-in-Oil-in-Water Emulsion Containing a Soluble Calcium Salt and Stabilized by Solid Particles 0.5 g of titanium dioxide modified with sodium laurel sulfate was added to coconut oil and mixed with stirring while heating until homogeneous to form an oil phase. During this, the mixture was heated to 30° C. Thereafter, 3.5 ml of a 5 wt. % calcium bicarbonate solution and 3.5 ml of the olive oil containing the modified titanium dioxide were mixed with a high-speed disperser at a stirring speed of 7,500 rpm and at 30° C. for 15 minutes to obtain a water-in-oil emulsion.

2 g of diatomaceous earth was added to 50 g of water to form a water phase. 2 ml of the water-in-oil emulsion obtained above and 2 ml of the water phase were mixed with a high-speed disperser at a stirring speed of 15,000 rpm and at 30° C. for 20 minutes to obtain a water-in-oil-in-water emulsion containing calcium ions.

(2) Preparation of a Water-in-Oil-in-Water Emulsion Containing a Soluble Phosphate Salt and Stabilized by Solid Particles 0.6 g of hydroxyapatite was added to 10 g of soybean oil and mixed with stirring while heating until homogeneous to form an oil phase. During this, the mixture was heated to 30° C. Thereafter, 1 ml of a 3.6 wt. % ammonium hydrogen phosphate solution and 4 ml of the soybean oil containing the hydroxyapatite were mixed with a high-speed disperser at a stirring speed of 1,200 rpm and at 30° C. for 70 minutes to obtain a water-in-oil emulsion.

0.8 g of magnesium silicate was added to 20 g of water and stirred until homogeneous to form a water phase. 1.5 ml of the water-in-oil emulsion obtained above and 1 ml of the water phase were mixed with a high-speed disperser at a stirring speed of 12,000 rpm and at 30° C. for 45 minutes to obtain a water-in-oil-in-water emulsion containing phosphate ions.

(3) Preparation of a Mouth Wash Base

A mouth wash base was prepared by the known procedure using the following ingredients: a humectant, a surfactant, a thickening agent, a sweetener, a preservative, an active additive, a flavor and the like.

(4) Preparation of a Mouth Wash Containing Both a Soluble Calcium Slat and a Soluble Phosphate Salt 3 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being 5:3) and 2 g of the mouth wash base were mixed with a high-speed disperser at a stirring speed of 8,000 rpm and at 30° C. for 35 minutes to produce a mouth wash product.

Tests showed that a rate of enamel remineralization provided by the mouth wash in this Example was 17 times that provided by the conventional mouth wash.

The above description is merely preferred embodiments of the present disclosure and not intended to limit the scope of the present disclosure. Any simple modifications, changes, and equivalent structures that are based on the principle and concept of the present disclosure shall all be within the scope of the present disclosure.

What is claimed is:

1. A method for making a composition for enamel regeneration, comprising steps of:
   (1) preparation of a water-in-oil-in-water emulsion containing a soluble calcium salt and stabilized by solid particles, the preparation of the emulsion comprising:
      adding organic and/or inorganic micro-nano particles suitable for stabilizing emulsions to a natural oil of plant, animal or mineral origin, or to a synthetic oil produced from petrochemical products or products extracted from natural sources and mixing with stirring at 30 to 80° C. until homogeneous to form an oil phase, wherein, a mass ratio of the micro-nano particles to the natural or synthetic oil is from 0.1:100 to 25:100, and either the natural oil or the synthetic oil is suitable for oral care or for use in the preparation of a toothpaste, mouth wash or enamel restoring gel;
      adding to water a substance capable of dissolving in water or alcohol and of supplying free calcium ions so as to form an aqueous solution with a calcium ion concentration of 0.1 to 60%;
      mixing the aqueous solution with the oil phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil emulsion;
      adding to water organic and/or inorganic micro-nano particles suitable for stabilizing emulsions to form a water phase, wherein, a mass ratio of the micro-nano particles to the water is from 0.1:100 to 25:100; and
      mixing the water-in-oil emulsion with the water phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil-in-water emulsion containing a soluble calcium salt;
   (2) preparation of a water-in-oil-in-water emulsion containing a soluble phosphate salt and stabilized by solid particles, the preparation of the emulsion comprising:
      adding organic and/or inorganic micro-nano particles suitable for stabilizing emulsions to a natural oil of plant, animal or mineral origin, or to a synthetic oil produced from petrochemical products or products extracted from natural sources and mixing with stirring at 30 to 80° C. until homogeneous to form an oil phase, wherein, a mass ratio of the micro-nano particles to the natural or synthetic oil is from 0.1:100 to 25:100, and either the natural oil or the synthetic oil is suitable for oral care or for use in the preparation of a toothpaste, mouth wash or enamel resorting gel;
      adding to water a substance capable of dissolving in water or alcohol and of supplying free phosphate ions, hydrogen phosphate, and/or dihydrogen phosphate so as to form an aqueous solution, with a concentration of the free phosphate ions, hydrogen phosphate, and/or dihydrogen phosphate being 0.1 to 60%;

mixing the aqueous solution with the oil phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil emulsion;

adding to water organic and/or inorganic micro-nano particles suitable for stabilizing emulsions to form a water phase, wherein, a mass ratio of the micro-nano particles to the water is from 0.1:100 to 25:100; and mixing the water-in-oil emulsion with the water phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil-in-water emulsion containing a soluble phosphate salt; and (3) preparation of a mouth wash, toothpaste or enamel restoring gel containing both a soluble calcium salt and a soluble phosphate salt, the preparation thereof comprising:

mixing the water-in-oil-in-water emulsion containing a soluble calcium salt and the water-in-oil-in-water emulsion containing a soluble phosphate salt with a mouth wash, toothpaste, or enamel restoring gel base, with a stirring speed of 10 to 24,000 rpm at 30 to 80° C. for 0.5 to 120 minutes to obtain a mouth wash, toothpaste or enamel restoring gel containing both a soluble calcium salt and a soluble phosphate salt, wherein, a molar ratio of the calcium ions in the water-in-oil-in-water emulsion containing a soluble calcium salt to the phosphate ions in the water-in-oil-in-water emulsion containing a soluble phosphate salt is 5:3, and the ratio of the mass of the water-in-oil-in-water emulsion containing a soluble calcium salt and the water-in-oil-in-water emulsion containing a soluble phosphate salt to mass of the mouth wash, toothpaste or enamel restoring gel base is from 1:19 to 19:1.

2. The method according to claim 1, wherein, the micro-nano particles used in the steps (1) and (2) are one or more of silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, zeolite, polyethylene, polystyrene, a polyacrylic resin, a natural vegetable powder, a surface modified natural vegetable powder, and cellulose and a functionalized amphiphilic derivative thereof; or, the micro-nano particles are one or more of silicon dioxide, aluminium oxide, bioactive glass, calcium carbonate, calcium silicate, calcium phosphate, hydroxyapatite, zinc oxide, titanium dioxide, magnesium carbonate, magnesium hydroxide, diatomaceous earth, montmorillonite, hydrotalcite, mica, attapulgite, and zeolite modified with a silane coupling agent, a titanate coupling agent or a surfactant;

wherein, the surfactant for modifying the zeolite is any amphiphilic surfactant suitable for use in the preparation of oral cleaning or care products.

3. The method according to claim 1, wherein, the oil used in the steps (1) and (2) is more or of rapeseed oil, peanut oil, cannabis oil, corn oil, olive oil, camellia oil, palm oil, sunflower oil, sunflower oil, soybean oil, sesame oil, linseed oil, grape seed oil, walnut oil, peony seed oil, coconut oil, edible paraffin, turpentine, lard oil, beef fat, mutton fat, fish oil, oviductus ranae, snake oil, silicone oil, linear alkane, lipil, and alcohol non-miscible in water.

4. The method according to claim 1, wherein, the substance capable of supplying free calcium ions is one or more of calcium chloride, calcium carbonate, calcium hydroxide, calcium oxide, calcium phosphate, calcium nitrate, calcium gluconate, calcium bicarbonate, calcium bisulfate, and calcium lactate.

5. The method according to claim 1, wherein, the substance capable of supplying free phosphate ions, hydrogen phosphate, and/or dihydrogen phosphate is one or more of potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate.

6. The method according to claim 2, wherein, the surfactant for modifying the zeolite is selected from the group consisting of sodium lauryl sulfate, sodium dodecyl benzene sulfate, sodium lauryl sulfate, a glucoside nonionic surfactant, betaine, and combinations thereof.

* * * * *